(12) United States Patent
Koyrakh et al.

(10) Patent No.: US 10,082,395 B2
(45) Date of Patent: Sep. 25, 2018

(54) SCALING OF ELECTRICAL IMPEDANCE-BASED NAVIGATION SPACE USING INTER-ELECTRODE SPACING

(71) Applicants: Lev Abramovich Koyrakh, Plymouth, MN (US); Sean Morgan, Minneapolis, MN (US)

(72) Inventors: Lev Abramovich Koyrakh, Plymouth, MN (US); Sean Morgan, Minneapolis, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 983 days.

(21) Appl. No.: 13/644,233

(22) Filed: Oct. 3, 2012

(65) Prior Publication Data

US 2014/0095105 A1   Apr. 3, 2014

(51) Int. Cl.
| | | |
|---|---|---|
| G01C 21/00 | (2006.01) | |
| A61B 5/06 | (2006.01) | |
| A61B 34/20 | (2016.01) | |
| A61B 18/14 | (2006.01) | |
| A61B 18/00 | (2006.01) | |

(52) U.S. Cl.
CPC ............. *G01C 21/00* (2013.01); *A61B 5/065* (2013.01); *A61B 18/1492* (2013.01); *A61B 2018/00577* (2013.01); *A61B 2034/2053* (2016.02)

(58) Field of Classification Search
CPC ..... G01C 21/00; A61B 5/065; A61B 18/1492; A61B 2018/00577; A61B 2019/5253

USPC .......................... 702/152; 600/574, 374, 509
See application file for complete search history.

(56) References Cited

U.S. PATENT DOCUMENTS

| | | | |
|---|---|---|---|
| 6,233,476 | B1 | 3/2001 | Strommer et al. |
| 6,498,944 | B1 | 12/2002 | Ben-Haim et al. |
| 6,690,963 | B2 | 2/2004 | Ben-Haim et al. |
| 6,788,967 | B2 | 9/2004 | Ben-Haim et al. |
| 7,197,354 | B2 | 3/2007 | Sobe |
| 7,263,397 | B2 | 8/2007 | Hauck et al. |
| 7,386,339 | B2 | 6/2008 | Strommer et al. |
| 7,536,218 | B2 | 5/2009 | Govari et al. |
| 2004/0116804 | A1* | 6/2004 | Mostafavi ..................... 600/428 |
| 2004/0201863 | A1* | 10/2004 | Bailey et al. .................. 358/1.2 |
| 2007/0016007 | A1* | 1/2007 | Govari ................. A61B 5/0538 |
| | | | 600/424 |
| 2007/0060833 | A1 | 3/2007 | Hauck |

(Continued)

OTHER PUBLICATIONS

Raul san Jose Estepar, Local Structure Tensor for Multiminentional Signal Processin : Applications to Medical Image Analysis, UCL Presses, Belgium (2007).*

(Continued)

*Primary Examiner* — Mohamed Charioui
*Assistant Examiner* — Catherine Rastovski
(74) *Attorney, Agent, or Firm* — Dykema Gossett PLLC

(57) ABSTRACT

An algorithm to correct and/or scale an electrical current-based coordinate system can include the determination of one or more global transformation or interpolation functions and/or one or more local transformation functions. The global and local transformation functions can be determined by calculating a global metric tensor and a number of local metric tensors. The metric tensors can be calculated based on pre-determined and measured distances between closely-spaced sensors on a catheter.

19 Claims, 6 Drawing Sheets

(56) References Cited

U.S. PATENT DOCUMENTS

| | | | |
|---|---|---|---|
| 2008/0095465 A1* | 4/2008 | Mullick et al. | 382/284 |
| 2008/0221425 A1* | 9/2008 | Olson et al. | 600/407 |
| 2008/0317317 A1* | 12/2008 | Shekhar et al. | 382/131 |
| 2012/0184863 A1* | 7/2012 | Harlev | A61B 5/7475 600/509 |
| 2013/0066193 A1 | 3/2013 | Olson et al. | |

OTHER PUBLICATIONS

Bennick, H.E. et al., "Warping a Neuro-Anatomy Atlas on 3D MRI Data with Radial Basis Functions", IFMBE Proceedings, vol. 15, Part 2, 28-32, 2007.

Bookstein, F.L. "Principal warps: Thin-plate splines and the decomposition of deformations", IEEE Trans. Pattern Analysis and Machine Intelligence, 11(6):567585, Jun. 1989.

Carr, J.C., et al., "Reconstruction and Representation of 3D Objects with Radial Basis functions", SIGGRAPH '01 Proceedings of the 28th annual conference on Computer graphics and interactive techniques, 2001.

Chui, H., et al., "A new point matching algorithm for non-rigid registration", CVIU, 2003.

Donato, G., et al., "Approximate thin-plate spline mappings", ECCV, 2002.

Kruskal, J.B., et al., "Multidimensional Scaling", 1:7-29, Sage Publications, 1977.

Landau, L.D., et al., "The Classical Theory of Fields", Butterworth-Heinemann, 4th ed., 230-233, Jan. 15, 1980.

Masson, L., et al., "Tracking 3D objects using flexible models", BMVC, 2005.

Misner, et al., "Graviatation", W.H. Freeman: First Edition, 304-332, Sep. 15, 1973.

O'Rourke, Joseph, "Computational Geometry in C", 1-5:1-193, Second Edition, Cambridge University Press, 1998.

Shlens, J.A., "A Tutorial on Principal Component Analysis", Salk Institute for Biological Studies, 2005.

Wahba, Grace, "Spline Models for Observational Data", SIAM, Philadelphia, Pennsylvania, 1-20, 45-65, 1990.

Will, Todd, "Introduction to the Singular Value Decomposition".

Wittkampf, F. H., et al. "LocaLisa: New Technique for Real-Time 3-Dimensional Localization of Regular Intracardiac Electrodes", Circulation, 99:1312-1317, 1999.

Bennink, H.E. et al., "Warping a Neuro-Anatomy Atlas on 3D MRI Data with Radial Basis Functions", IFMBE Proceedings, vol. 15, Part 2, 28-32, 2007.

Will, Todd, "Introduction to the Singular Value Decomposition", 2003.

* cited by examiner

SCALING OF ELECTRICAL IMPEDANCE-BASED NAVIGATION SPACE USING INTER-ELECTRODE SPACING

BACKGROUND OF THE INVENTION a. Field of the Invention

The instant disclosure relates to positioning and navigation of a medical device. More specifically, the instant disclosure relates to correction and scaling of a coordinate system for a positioning and navigation system.

b. Background Art

Various systems are known for determining the position and orientation (P&O) of a medical device in a human body, for example, for visualization and navigation purposes. One such system is known as an electrical field-based or impedance-based positioning system. Electrical field-based systems generally include one or more pairs of body surface electrodes (e.g., patches) outside a patient's body, a reference sensor (e.g., another patch) attached to the patient's body, and one or more sensors (e.g., electrodes) attached to the medical device. The patch electrode pairs can be adjacent, linearly arranged, or associated with respective axes of a coordinate system for such a positioning system. The system can determine P&O by applying a current across pairs of patch electrodes, measuring respective voltages induced at the device electrodes (i.e., with respect to the reference sensor), and then processing the measured voltages.

Because electrical field-based systems employ electrical current flow in the human body, the coordinate systems can be non-homogenous, anisotropic, and not orthonormal (i.e., the basic vectors of the coordinate system are not guaranteed to be at right angles to one another or to have proper unit lengths). As a result, geometries and representations that are rendered based on position measurements using such systems may appear distorted relative to actual images of subject regions of interest.

BRIEF SUMMARY OF THE INVENTION

To address one or more of the problems set forth above, an electrical field-based coordinate system can be corrected through an algorithm including one or more global transformation or interpolation functions and/or one or more local transformation functions. The algorithm may involve or allow for the application of one or more methods for determining the position of a medical device comprising a first position sensor and a second position sensor, and/or one or more methods for determining the location of a sensor.

An embodiment of one such method can include a number of steps. A first step can include detecting respective positions of the first sensor and the second sensor in a first coordinate system. Another step can include measuring the distance between the respective first positions. Another step can include determining a transformation function according to a known distance between the first sensor and the second sensor and according to the measured distance between the first position and the second position, wherein the transformation function relates a set of coordinates in the first coordinate system to a set of coordinates in a second coordinate system. Another step can include measuring a position a third sensor in the first coordinate system, and another step can include applying the transformation function to the measured position of the third sensor to relate the measured position of the third sensor to the second coordinate system.

An embodiment of a second method can also include a number of steps. A first step can include determining a global transformation function that relates a set of coordinates in a first coordinate system to a corresponding set of coordinates in a second coordinate system such as, for example only, as in the first method above. Another step can include dividing a portion of the space covered by the second coordinate system into a plurality of local volumes. Another step can include determining a local transformation function for at least one of the plurality of local volumes, each local transformation function determined according to a plurality of position measurements in the first coordinate system or the second coordinate system within a respective local volume. Another step can include establishing an interpolation function according to the local transformation function, the interpolation function configured to relate a set of coordinates in the first coordinate system into a corresponding set of coordinates in a third coordinate system. Another step can include receiving a signal from a sensor indicative of a position of the sensor within the first coordinate system. Another step can include applying the interpolation function to the position to determine a position of the sensor in the third coordinate system.

A system may be configured to apply an algorithm including one or more global transformation or interpolation functions and/or one or more local transformation functions for determining the location of a first medical device comprising a first position sensor. An embodiment of such a system may comprise an electronic control unit (ECU) comprising a processor, a computer-readable memory coupled to the processor, and instructions stored in the memory configured to be executed by the processor. The processor may be configured to execute the instructions to perform a number of steps. A first step can include detecting respective positions of a first sensor and a second sensor in a first coordinate system. Another step can include measuring the distance between the respective positions. Another step can include determining a transformation function according to a known distance between the first sensor and the second sensor and according to the measured distance between the respective positions, wherein the transformation function relates a set of coordinates in the first coordinate system to a set of coordinates in a second coordinate system.

DETAILED DESCRIPTION OF THE INVENTION

Various embodiments are described herein with respect to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
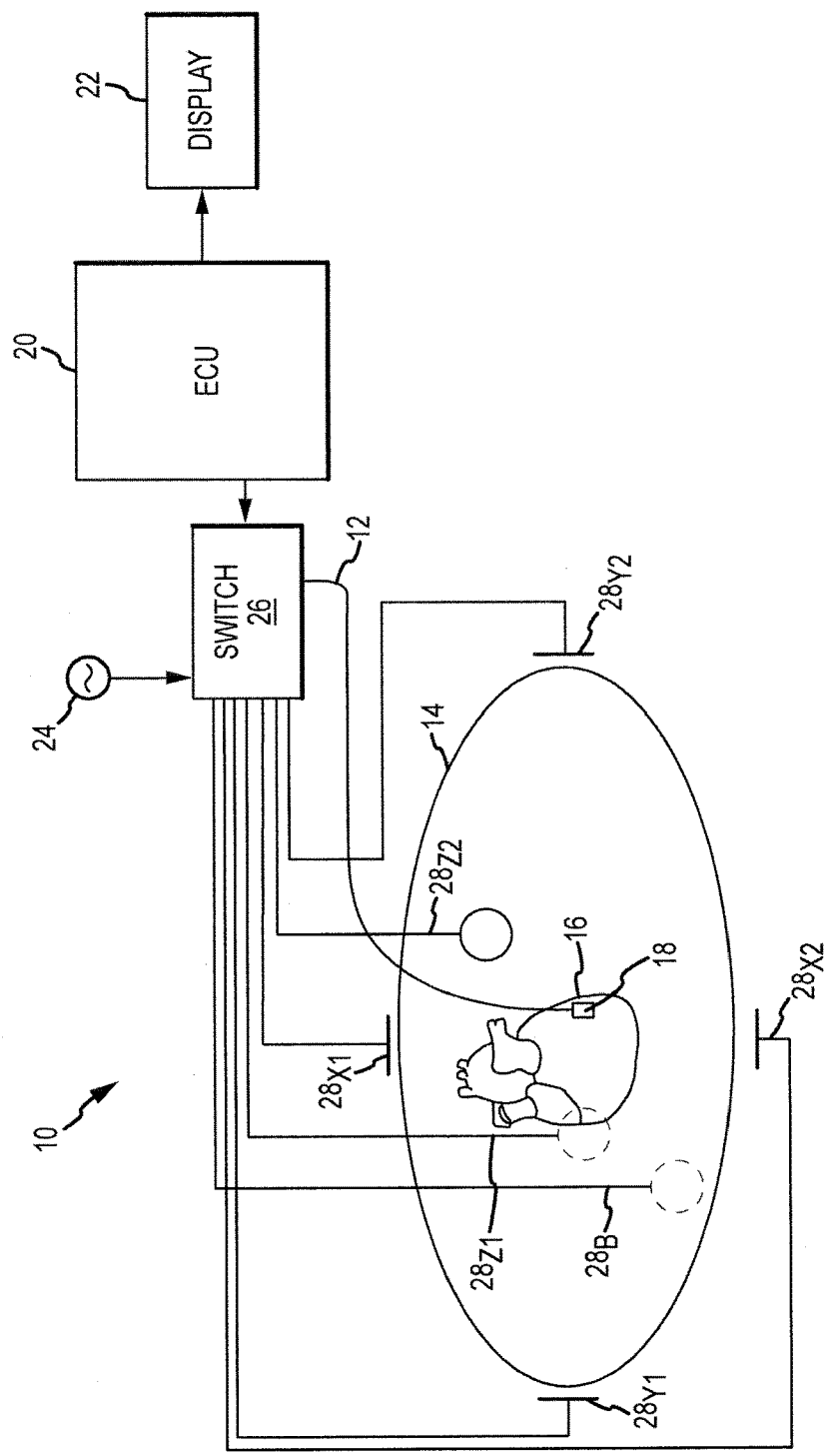
FIG. 1 is a schematic and block diagram view of a medical device mapping and navigation system.
Figure 2A:
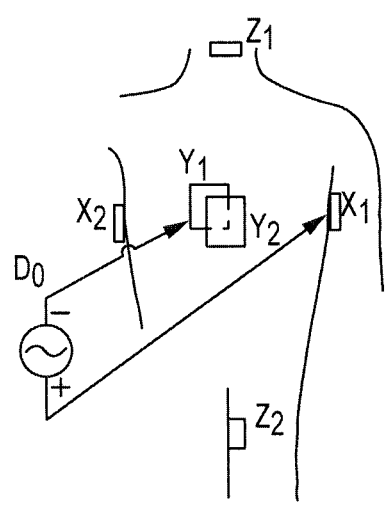
FIGS. 2A-2D are schematic diagrams of exemplary dipole pairs of driven body surface electrodes.
Figure 2B:
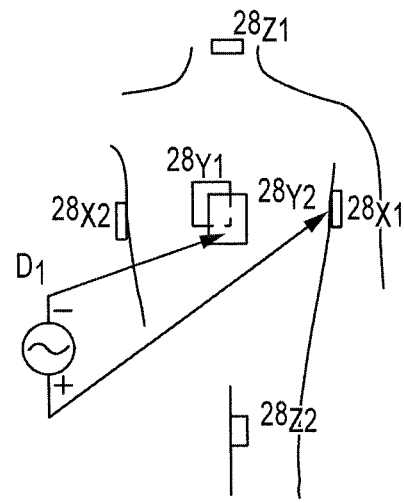
Figure 2C:
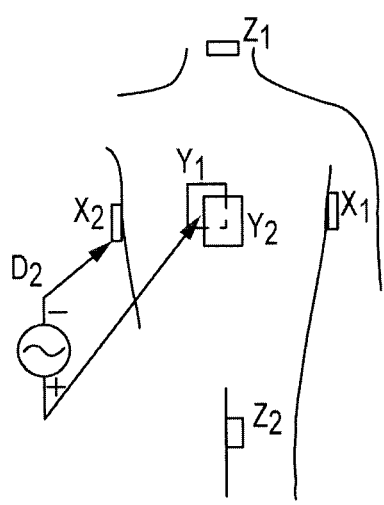
Figure 2D:
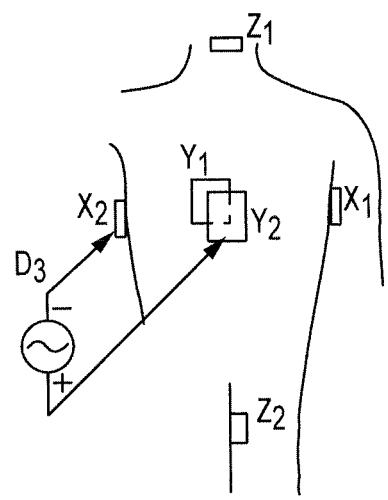

Referring now to the Figures, in which like reference numerals refer to the same or similar features in the various views, FIG. 1 is a schematic and diagrammatic view of an embodiment of a medical device mapping and navigation system 10. The system 10 is coupled with a catheter 12 that can be guided to and disposed in a portion of a body 14, such as a heart 16. The catheter 12 can include one or more sensors 18 for, e.g., determining a location within the system 10. The system 10 can include, at least in part, an electronic control unit (ECU) 20, a display 22, a signal generator 24, a switch 26, and a plurality of body surface electrode patches 28.

The mapping and navigation system 10 is provided for visualization, mapping, and/or navigation of internal body structures and may be referred to herein as "the navigation system." The navigation system 10 may comprise an electric field-based system, such as, for example, an ENSITE VELOCITY cardiac electro-anatomic mapping system running a version of ENSITE NAVX navigation and visualization technology software commercially available from St. Jude Medical, Inc., of St. Paul, Minn. and as also seen generally by reference to U.S. Pat. No. 7,263,397, or U.S. Patent Application Publication No. 2007/0060833 A1, both hereby incorporated by reference in their entireties as though fully set forth herein. In other exemplary embodiments, the navigation system 10 may comprise systems other than electric field-based systems. For example, the navigation system 10 may comprise a magnetic field-based system such as the CARTO system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the navigation system 10 may comprise a magnetic field-based system based on the MEDIGUIDE technology available from St. Jude Medical, Inc., and as generally shown with reference to one or more of U.S. Pat. Nos. 6,233,476; 7,197,354; and 7,386,339, the disclosures of which are hereby incorporated by reference in their entireties as though fully set forth herein. In yet another embodiment, the navigation system 10 may comprise a combination electric field-based and magnetic field-based system, such as, for example and without limitation, the system described in pending U.S. patent application Ser. No. 13/231,284, or the CARTO 3 system commercially available from Biosense Webster, and as generally shown with reference to U.S. Pat. No. 7,536,218, the disclosures of which are hereby incorporated by reference in their entireties as though set fully forth herein. In yet still other exemplary embodiments, the navigation system 10 may comprise or be used in conjunction with other commonly available systems, such as, for example and without limitation, fluoroscopic, computed tomography (CT), and magnetic resonance imaging (MRI)-based systems. For purposes of clarity and illustration only, the navigation system 10 will be described hereinafter as comprising an electric field-based system, such as, for example, the ENSITE NAVX system identified above.

The catheter 12 and sensors 18 may be provided for a variety of diagnostic and therapeutic purposes including, for example, electrophysiological studies, pacing, cardiac mapping, and ablation. In an embodiment, the catheter 12 can be an ablation catheter, mapping catheter, or other elongate medical device. The number, shape, orientation, and purpose of the sensors 18 may vary in accordance with the purpose of the catheter 12. For example, and as will be discussed in greater detail in conjunction with FIGS. 3A-5, in some embodiments a plurality of sensors 18 on a single catheter 12 may be used in conjunction with the methods described herein. In an embodiment, at least one sensor 18 can be an electrode. For purposes of illustration, the description below will be with respect to an embodiment in which the sensors 18 comprise one or more electrodes, but the disclosure is not limited to such an embodiment.

With the exception of the patch electrode $28_B$ called a "belly patch," the patch electrodes 28 are provided to generate electrical signals used, for example, in determining the position and orientation of the catheter 12 and in the guidance thereof. In one embodiment, the patch electrodes 28 are placed generally orthogonally on the surface of the body 14 and are used to create axes-specific electric fields within the body 14. For instance, in one exemplary embodiment, patch electrodes $28_{X1}$, $28_{X2}$ may be placed along a first (x) axis. Patch electrodes $28_{Y1}$, $28_{Y2}$ may be placed along a second (y) axis, and patch electrodes $28_{Z1}$, $28_{Z2}$ may be placed along a third (z) axis. Each of the patch electrodes 28 may be coupled to the multiplex switch 26. In an exemplary embodiment, the ECU 20 is configured, through appropriate software, to provide control signals to the multiplex switch 26 to thereby sequentially couple pairs of electrodes 28 to the signal generator 24. Excitation of each pair of electrodes 28 (e.g., in either orthogonal or non-orthogonal pairs) generates an electrical field within the patient's body 14 and within an area of interest such as the heart 16. Voltage levels at non-excited electrodes 28, which are referenced to the belly patch $28_B$, are filtered and converted and provided to the ECU 20 for use as reference values.

As noted above, one or more electrodes 18 are mounted in or on the catheter 12. In an exemplary embodiment, at least one of the electrodes 18 comprises a positioning electrode and is configured to be electrically coupled to the ECU 20. With a positioning electrode 18 electrically coupled to the ECU 20, the electrode 18 is placed within electrical fields created in the body 14 (e.g., within the heart 16) by exciting the patch electrodes 28. The positioning electrode 18 experiences voltages that are dependent on the position of the positioning electrode 18 relative to the locations of the patch electrodes 28. Voltage measurement comparisons made between the electrode 18 and the patch electrodes 28 can be used to determine the position of the positioning electrode 18 relative to the heart 16 or other tissue. Movement of the positioning electrode 18 proximate a tissue (e.g., within a chamber of the heart 16) may produce information regarding the geometry of the tissue. This information may be used, for example, to generate models and maps of anatomical structures. Information received from the positioning electrode 18 can also be used to display on a display device, such as display 22, the location and orientation of the positioning electrode 18 and/or a portion of the catheter 12 relative to the heart 16 or other tissue. Accordingly, among other things, the ECU 20 of the navigation system 10 provides a means for generating display signals used to the control display 22 and the creation of a graphical user interface (GUI) on the display 22.

The ECU 20 may comprise a programmable microprocessor or microcontroller, or may comprise an application specific integrated circuit (ASIC). The ECU 20 may include a an input/output (I/O) interface through which the ECU 20 may receive a plurality of input signals including, for example, signals generated by patch electrodes 28 and the positioning electrode 18 (among others), and generate a plurality of output signals including, for example, those used to control the display 22 and other user interface components. The ECU 20 may be configured to perform various functions, such as those described in greater detail above and below, with appropriate programming instructions or code (i.e., software). Accordingly, the ECU 20 can be programmed with one or more computer programs encoded on a computer-readable storage medium for performing the functionality described herein. For example, as will be described in conjunction with FIGS. 3A-5, the ECU 20 can be configured to execute logic to generate one or more transformation functions or interpolation functions to relate coordinates in a first coordinate system to coordinates in a second coordinate system.

In operation, as the patch electrodes 28 are selectively energized, the ECU 20 receives position signals (location information) from the catheter 12 (and particularly the positioning electrode 18) reflecting changes in voltage levels on the positioning electrode 18 and from the non-energized patch electrodes 28. The ECU 20 uses the raw positioning data produced by the patch electrodes 28 and positioning electrode 18 and may correct the data to account for respiration, cardiac activity, and other artifacts using known techniques. The corrected data may then be used by the ECU 20 in a number of ways, such as, for example and without limitation, to guide an ablation catheter to a treatment site, to create a model of an anatomical structure, to map electrophysiological data on an image or model of the heart 16 or other tissue generated or acquired by the ECU 20, or to create a representation of the catheter 12 that may be superimposed on a map, model, or image of the heart 16 generated or acquired by the ECU 20. Even after correcting for respiration, cardiac activity, and other artifacts, though, the coordinate system generated by the navigation system 10 can be non-orthonormal with local inconsistencies and variations. Thus, the ECU 20 may be configured to execute one or more algorithms or methods to relate coordinates in the native, electrical field-based coordinate system to a second coordinate system that may be orthonormal and may correct local inconsistencies and variations.

FIGS. 2A-2D show a plurality of exemplary non-orthogonal dipoles, designated $D_0$, $D_1$, $D_2$ and $D_3$, set in a first coordinate system A (i.e., the native coordinate system of the navigation system 10). For any desired axis, the potentials measured across an intra-cardiac positioning electrode 18 resulting from a predetermined set of drive (source-sink) configurations may be combined algebraically to yield the same effective potential as would be obtained by simply driving a uniform current along the orthogonal axes. Any two of the surface electrodes 28 may be selected as a dipole source and drain with respect to a ground reference, e.g., belly patch $28_B$, while the unexcited body surface electrodes measure voltage with respect to the ground reference. The positioning electrode 18 placed in heart 16 is also exposed to the field from a current pulse and is measured with respect to ground, e.g., belly patch $28_B$. In practice, a catheter or multiple catheters within the heart may contain multiple positioning electrodes 18 and each positioning electrode 18 potential may be measured separately.

Data sets from each of the patch electrodes and the positioning electrode 18 are used to determine the location of the positioning electrode 18 within heart 16. After the voltage measurements are made, a different pair of surface electrodes is excited by the current source and the voltage measurement process of the remaining patch electrodes and positioning electrode 18 takes place. The sequence occurs rapidly, e.g., on the order of 100 times per second in an embodiment. To a first approximation the voltage on the positioning electrode 18 within the heart bears a linear relationship with position between the patch electrodes that establish the field within the heart, as more fully described in U.S. Pat. No. 7,263,397 referred to above.

In summary, FIG. 1 shows an exemplary navigation system 10 that employs seven body surface electrodes (patches), which may be used for injecting current and sensing resultant voltages. Current may be driven between two patches at any time; some of those driven currents are illustrated in FIGS. 2A-2D. Measurements may be performed between a non-driven patch and, for example, belly patch $28_B$ as a ground reference. A patch bio-impedance, also referred to as a "patch impedance" may be computed according to the following equation:

$$BioZ[c \to d][e] = \frac{V_e}{I_{c \to d}} \quad (1)$$

where $V_e$ is the voltage measured on patch e and $I_{c \to d}$ a known constant current driven between patches c and d, where patches c, d, and e may be any of the patch electrodes 28. The position of an electrode may be determined by driving current between different sets of patches and measuring one or more patch impedances along with the voltage on the positioning electrode. In one embodiment, time division multiplexing may be used to drive and measure all quantities of interest. Position determining procedures are described in more detail in U.S. Pat. No. 7,263,397 and Publication 2007/0060833 referred to above, as well as other references.

As noted above, coordinate system A, based on electric fields generated by driving electric current through the patient's body, can be non-orthonormal and can have local variations and inconsistencies. Accordingly, the ECU 20 can be programmed with one or more algorithms and/or methods to generate one or more transformation and/or interpolation functions. The ECU 20 can additionally be programmed to apply the generated transformation/interpolation function(s) to coordinates in the first coordinate system A to relate the coordinates to a second coordinate system B. The second coordinate system B may be orthonormal, and may correct for local variations and inconsistencies in the electrical current-based electrical field.

Figure 3A:
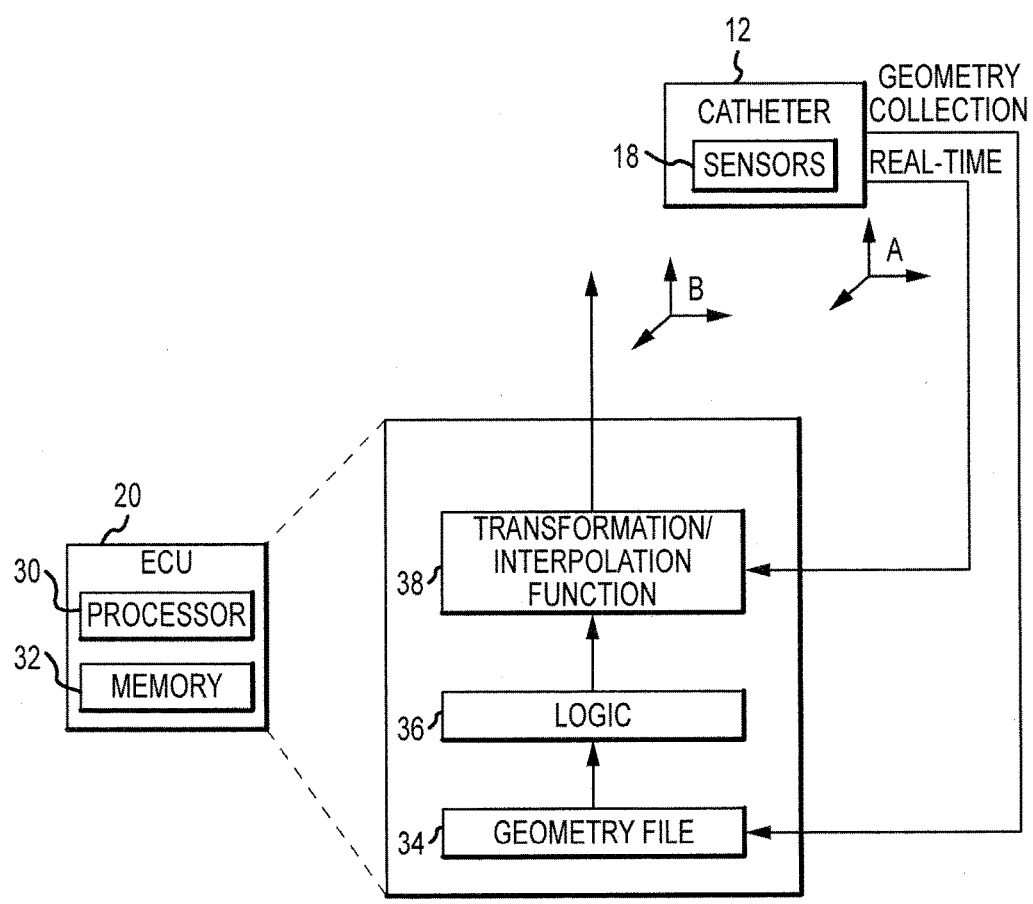
FIGS. 3A-3B are schematic and block diagram views of a portion of the system of FIG. 1.

FIG. 3A is a schematic and block diagram view of an embodiment of a portion of the navigation system 10. The system portion includes the ECU 20 and the catheter 12. The catheter 12, as shown, includes a number of electrodes 18 that provide signals to the ECU 20 indicative of their locations in the first coordinate system A. The ECU 20 can include a processor 30 and memory 32 containing a geometry file 34 and logic 36. The ECU 20 (i.e., the processor 30) can be configured to execute logic 36, and to apply one or more transformation/interpolation functions 38 stored in the memory 32, as described below.

The ECU 20 can be programmed to receive signals from the electrodes 18 on the catheter 12 and determine or detect the positions of the electrodes 18 according to those signals. The ECU 20 may also be programmed to determine the distance between neighboring electrodes 18 according to determined positions of those electrodes 18 ("measured inter-electrode spacings"), and to receive known actual distances between electrodes 18 ("known inter-electrode spacings"). Known inter-electrode spacings may be known from manufacturing specifications and input to the ECU 20 during an initial setup phase of the navigation system 10, may be stored on the catheter 12 (e.g., on an EEPROM or other portable storage device) and read by the ECU 20 during a setup phase, or may be otherwise known by the ECU 20. The ECU 20 may store a plurality of measured inter-electrode spacings, known inter-electrode spacings, and measured electrode positions in the geometry file 34. The contents of the geometry file 34 are described in greater detail in conjunction with FIG. 3B.

The ECU 20 (e.g., the processor 30) may be configured to execute instructions stored in the memory 32. In some embodiments, for example, the ECU 20 includes logic 36 for generating one or more transformation or interpolation functions 38 for relating coordinates in the coordinate system A to coordinates in the second coordinate system B. The ECU 20 can execute the logic 36 to generate one or more transformation/interpolation function(s) 38, to store the transformation/interpolation function(s) 38 in the memory 32, and further to apply the transformation/interpolation function(s) 38 to coordinates in the first coordinate system A to generate coordinates in the second coordinate system B. In effect, then, the ECU 20 can locate and display the position of the catheter 12 in the second coordinate system B substantially in real time, allowing for more accurate visualization of the catheter 12 with respect to pre-acquired images and models of the navigational space, such as a human heart and surrounding vasculature.

The logic 36 can be programmed to include one or more steps for generating the transformation/interpolation function(s) 38 according to the contents of the geometry file 34. Thus, by applying one or more algorithms and/or methods to the contents of the geometry file 34, the logic 36 can correct and/or lessen the effects of global and local distortions in the first coordinate system A to allow the ECU 20 to determine the position of the catheter 12 in the second coordinate system B, which may be orthonormal and/or relatively free of global and local distortions.

Figure 3B:
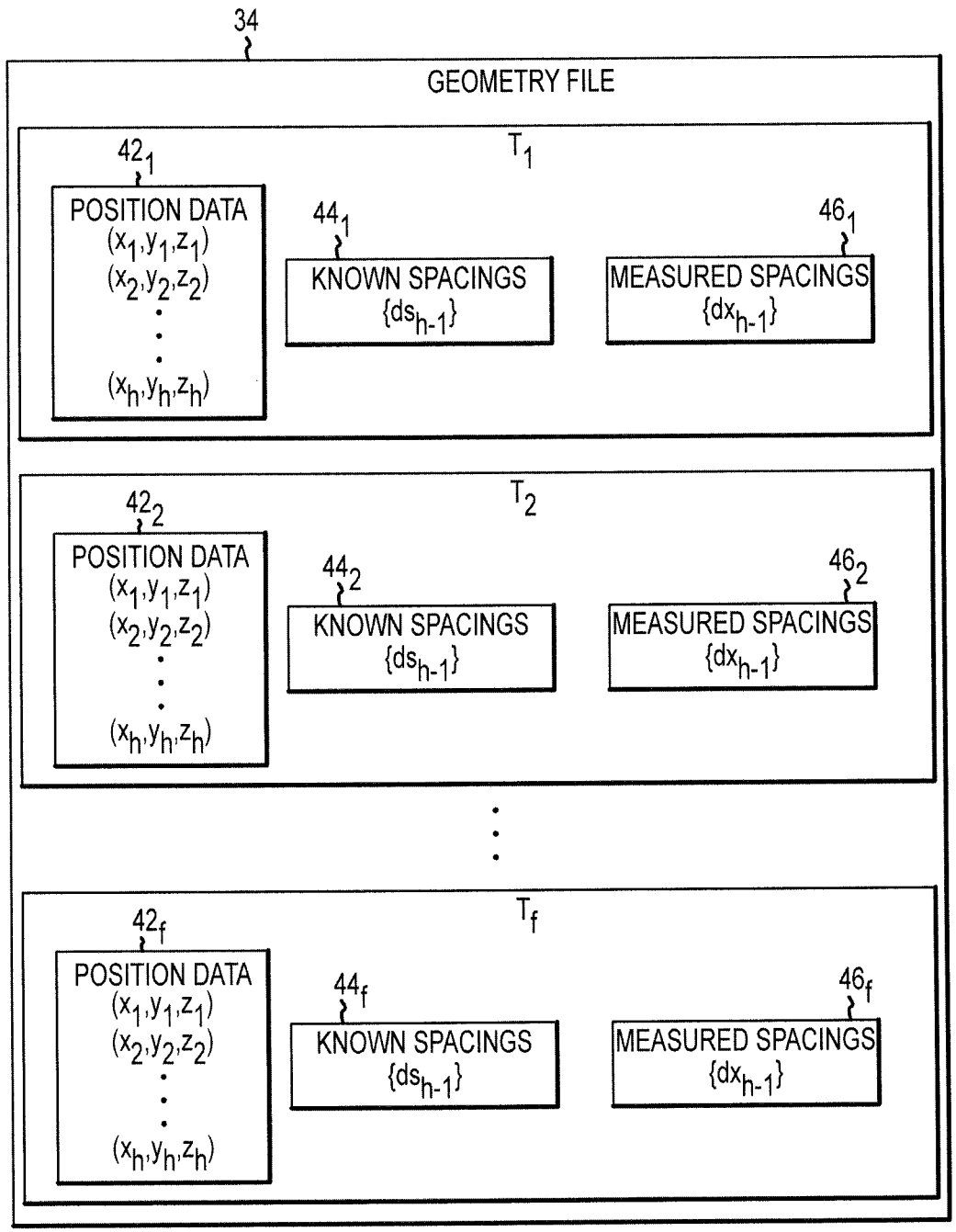

FIG. 3B is a block diagram view of an exemplary geometry file 34 that includes data blocks for a number f of collection times, namely, $T_1, T_2, \ldots, T_f$. For each collection time T, the geometry file 34 can include position data 42, a set of known inter-electrode spacings 44, and a set of measured inter-electrode spacings 46. Each collection time T may correspond to data collected at the same time or within a short time period. Thus, the geometry file 34 shown may be the result of a geometry collection step, as described in conjunction with FIGS. 4 and 5. Each block of positioning data 42 can include a measured location (in the native coordinate system A) for each of the electrodes 18. Thus, for a catheter with h positioning electrodes 18, the sensor data 42 can include h locations (i.e., h sets of coordinates) in the native coordinate system A for each collection time T.

The known inter-electrode spacings 44 are, as noted above, the predetermined distances between the electrodes 18. As noted above, the known inter-electrode spacings 44 may be input during an initial setup phase (e.g., to the memory 32), may be stored on the catheter 12 (e.g., on an EEPROM or other portable storage device) and read during a setup phase, or may be known to the ECU 20 in some other way. The measured inter-electrode spacings 46 are the distances between the positions of adjacent electrodes, according to the coordinates in the position data 42 for that time stamp T. For example, the measured inter-electrode spacings $46_1$ can be determined based on the contents of the sensor data $42_1$, the measured inter-electrode spacings $46_2$ can be determined based on the contents of the sensor data $42_2$, and so on.

The embodiment of the geometry file 34 shown is exemplary only. The present disclosure is not limited to a particular content or format of the geometry file 34. For example, though the geometry file 34 is shown with an equal number (h−1) of inter-electrode spacings for each collection time T, this need not be the case. Different numbers of inter-electrode spacings may be measured during different collection times for a number of reasons, and some electrode position measurements may be discarded as inaccurate or distorted. Accordingly, the number of electrode positions collected for each collection time T also need not be equal among all collection times T.

As noted above, the ECU 20 may be configured to execute one or more algorithms or methods for relating coordinates in the native coordinate system A to a second coordinate system B. An outline for one such algorithm is below, and two methods of executing the outlined algorithm (or parts thereof) are discussed in conjunction with FIGS. 4 and 5, respectively.

Algorithm Outline. One way to scale and/or correct a coordinate system for an electrical field- or impedance-based mapping and navigation system is to use the measured (i.e., measured with the navigation system) and known (i.e., pre-determined) inter-electrode spacings for characterizing the geometry of the electrical field. The algorithm can compute global and local metric tensors that describe the intrinsic geometry generated by the electrical fields of the mapping and navigation system. The global metric tensor can be used for constructing a global coordinate system, and the local metric tensors can be used for computing local geometry corrections. Finally, an interpolation function can be used to construct a map between the electrical field measurements and the locations of the catheter electrodes in a corrected coordinate system.

In some embodiments, the algorithm includes the following steps, each of which is further described in the following sections:

1. Collect a plurality of data points representing positions in the first coordinate system with a plurality of electrodes on a catheter and measure inter-electrode spacings according to those positions.

2. Based on the collected positions and measured inter-electrode spacings, compute a global metric tensor.

3. Construct a global coordinate system using the global metric tensor.

4. Divide the global space into local volume elements.

5. Compute a local metric tensor for one or more local volume elements.

6. Connect the centers of neighboring local volume elements for which local metric tensors have been computed.

7. Find the equilibrium locations of one or more local volume element centers based on the connections between volume element centers and on the local metric tensors.

8. Compute a map from the original coordinate system to a second coordinate system according to the original centers of the local volume elements and the equilibrium locations.

Though specific steps one (1) through eight (8) are noted above and discussed below, the methods and systems herein are not limited to such steps. Instead, in embodiments, other steps may be performed in addition to, or in lieu of, steps one (1) through eight (8).

Figure 4:
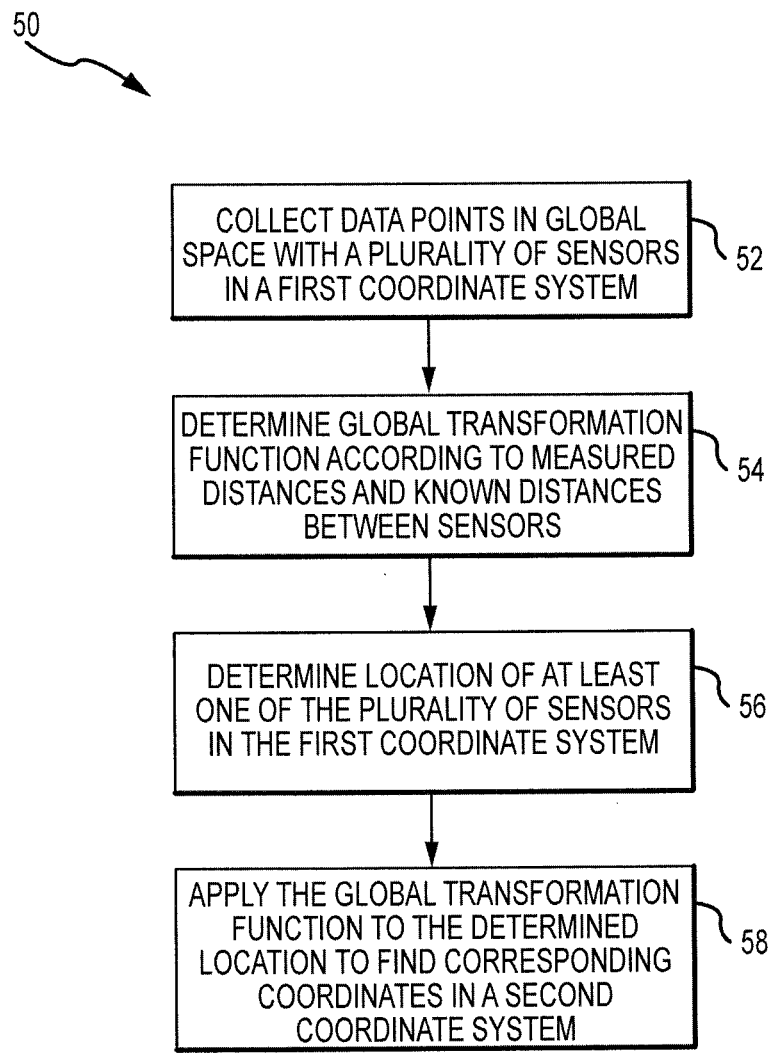
FIG. 4 is a flow chart illustrating an exemplary embodiment of a method for determining the position of a medical device.
Figure 5:
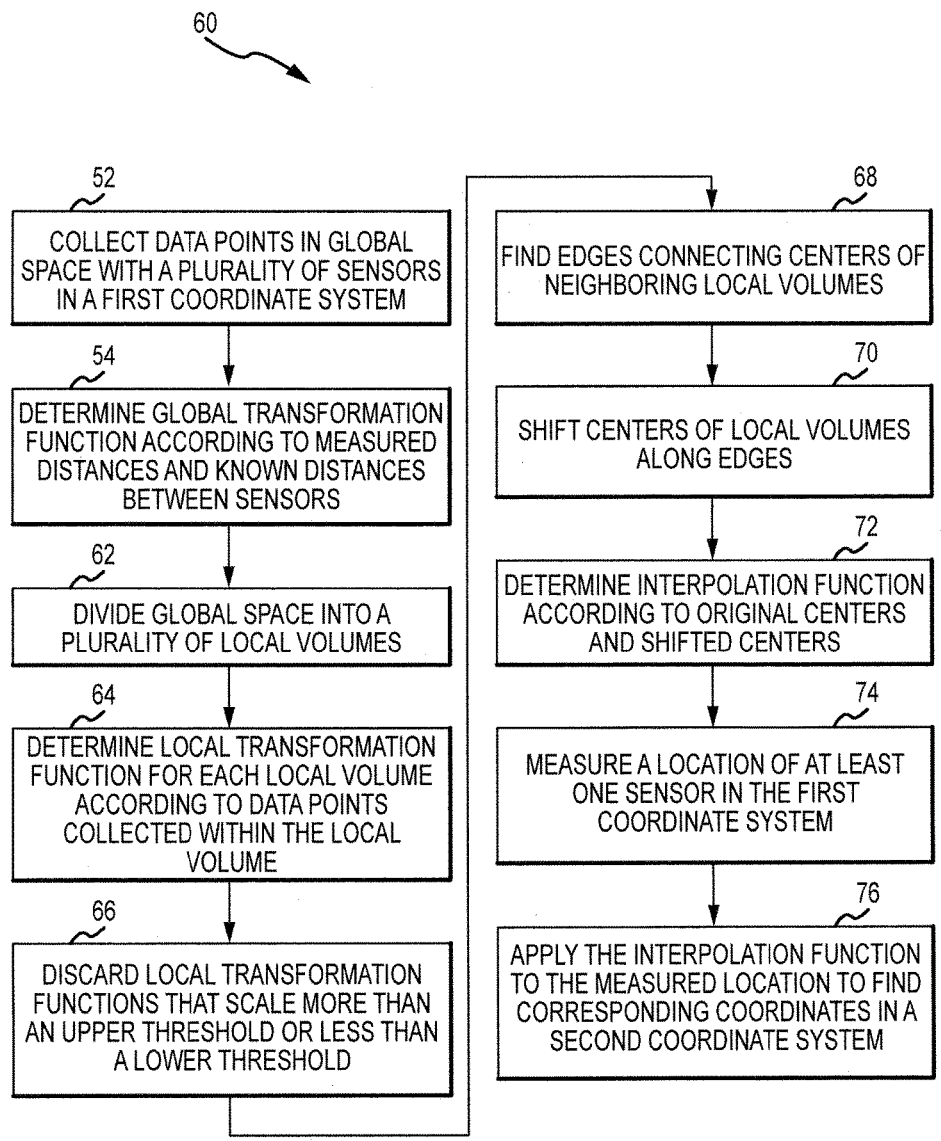
FIG. 5 is a flow chart illustrating another exemplary embodiment of a method for determining the position of a medical device.

FIGS. 4 and 5 are flow charts illustrating first and second exemplary methods 50, 60 for determining the position of a medical device. The methods 50, 60 involve scaling and/or correcting a first coordinate system to find coordinates in a second coordinate system based on certain portions of the above-outlined algorithm. The method illustrated in FIG. 4 includes a global transformation of the entire first coordinate system (i.e., steps 1 through 3 briefly described above). The method illustrated in FIG. 5 also includes a global transformation, and additionally includes one or more local transformations to correct local distortions in the first coordinate system (i.e., steps 1 through 8 briefly described above).

Coordinate System Nomenclature. The algorithm (and parts of the first and second methods 50, 60) includes the determination and use of electrode locations and inter-electrode spacings in several different coordinate systems. The coordinate system of the navigation system, before any correction by the algorithm, may be referred to as the native coordinate system, unsealed coordinate system, or field-based or impedance-based coordinate system. The coordinate system resulting from the application of a global transformation function to the native coordinate system may be referred to as the global coordinate system. The coordinate system resulting from the application of one or more local transformation functions and/or an interpolation function may be referred to as the corrected coordinate system. The coordinate system for a subspace within the broader nagivational space may be referred to as a local coordinate system. In addition, at multiple times during the algorithm, a coordinate system may be rotated temporarily for computation. Thus, references to the "rotated" coordinate system may refer to rotations of the native coordinate system, global coordinate system, corrected coordinate system, or a local coordinate system, depending on the context. Furthermore, this disclosure may refer to first, second, and third coordinate systems. The first, second, and third coordinate systems may be any of the native, global, and corrected coordinate systems, depending on context.

The first and second methods 50, 60 will be described with respect to an electrical field- or impedance-based mapping and navigation system. It should be understood, though, that the methods are not limited to such systems. Lower-case coordinates {x,y,z} are used herein to designate three-dimensional (3D) locations in the native coordinate system of the navigation system. In contrast, upper-case coordinates {X, Y, Z} are used to designate 3D locations in an orthonormal coordinate system, which may be the global coordinate system or the corrected coordinate system.

In vector notation, native coordinate system coordinates are denoted as:

$$\vec{x} = \{x^1, x^2, x^3\} = \{x,y,z\} \quad (2)$$

and orthonormal coordinates (in either the global or corrected coordinate system) are denoted as:

$$\vec{X} = \{X^1, X^2, X^3\} = \{X,Y,Z\}. \quad (3)$$

A goal of the methods of FIGS. 4 and 5 is to define a map between the first, native coordinate system and a second, orthonormal coordinate system:

$$\vec{X} = f(\vec{x}) \quad (4)$$

Data Collection. Referring to FIG. 4, the first method 50 can begin with a step 52 of collecting a plurality of data points with, for example, a plurality of sensors and a mapping and navigation system throughout the first coordinate system (i.e., the native coordinate system A of the mapping and navigation system). This step may be referred to as "geometry collection." In an embodiment, the sensors can be positioning electrodes for use with an electrical current-based mapping and navigation system, but other types of sensors may be used. The following description of the first and second methods 50, 60, will be with reference to an embodiment in which the sensors used comprise positioning electrodes, but the first and second methods 50, 60, are not limited to such an embodiment.

Geometry collection may comprise moving a catheter (e.g., such as the catheter 12 in FIGS. 1 and 3A) equipped with several electrodes (e.g., electrodes 18) throughout the navigational space of the mapping and navigation system and detecting the positions of the electrodes at a number of locations according to, e.g., impedance calculations as detailed above and as known in the art. Geometry collection may also include measuring the distances between detected electrode positions for adjacent electrodes—i.e., measuring inter-electrode spacings. Where the mapping and navigation system is to be used for a procedure on a patient's heart, for example, geometry collection may include collecting position information within the heart and surrounding vasculature. The result of geometry collection can be a data structure stored in a file, which contains information about collected data. An example of such a data structure is shown as the geometry file 34 in FIG. 3B. Using the information in the geometry file, one or more transformation or interpolation functions can be computed to create a second coordinate system for more accurately determining the position of a medical device.

In an embodiment, some of the collected data points may be discarded if they appear to be inaccurate or unreliable. For example, measured inter-electrode spacings that are smaller than a certain threshold or larger than another threshold may be discarded (as may the underlying position measurements). In an embodiment, such as data collected in a human heart, the lower threshold can be set at 4 mm. The upper threshold can be a number, or can be related to an expected value. For example, inter-electrode distances more than two (2) standard deviations greater than the mean measured inter-electrode spacing can be discarded. In an embodiment, the upper and/or lower thresholds may be determined according to known inter-electrode spacings.

Global Geometry Correction. After data has been collected to populate the geometry file, the first method 50 can continue to a step 54 of determining a global transformation function according to the measured inter-electrode spacings and known inter-electrode spacings. The global transformation function can be a linear transformation. Thus, a goal of the global geometry correction is to find the best fit linear transformation:

$$\vec{X} = C\vec{x}, \quad (5)$$

where C is the transformation matrix $C_i^{i'}$:

$$X^{i'} = \sum_{i=1}^{3} C_i^{i'} x^i \equiv C_i^{i'} x^i. \quad (6)$$

For brevity, the first relationship in equation (6) is written without summation signs, which are implied over the repeating upper and lower indices (Einstein's convention).

The upper and lower indices used in equation (6) above, together with the primed indices notation, provide a convenient way for tracking the transformation flow. For example, the inverse of equation (5) is given by $$(C^{-1})_{i'}^i X^{i'} = x^i, \quad (7)$$

where by definition $$(C^{-1})_{i'}^i = (C_i^{i'})^{-1}, \quad (8)$$

so that $$(C^{-1})_{i'}^i C_j^{i'} = \delta_j^i, \quad (9)$$

where $\delta_i^j$ is the Kronecker delta, which is defined by the equations:

$\delta_i^j = 1$, if i=j, $\delta_i^j = 0$, if i≠j.

One transformation matrix C that may be used is a so-called metric tensor, applied to the entire native coordinate system, referred to herein as a global metric tensor.

Metric Tensor Overview. Before proceeding to a description of how to compute a global metric tensor, the basic concepts of Riemannian geometry, also known as differential geometry, will first be briefly discussed. The main idea of Riemannian geometry is that a geometry can be fully described in terms of distance measurements between closely spaced locations. In intracardiac navigation, the space can be defined by a plurality of position measurements taken by a mapping and navigation system with a plurality of closely-spaced electrodes.

If {x,y,z} is used to define the location of each of a plurality of electrodes on a catheter then, for closely spaced electrodes on the catheter, a measured inter-electrode spacing between two electrodes can be denoted $d\vec{x} = \{dx^1, dx^2, dx^3\} = \{dx, dy, dz\}$. Thus, for a position associated with a first electrode, $\{x_1, y_1, z_1\}$ and a position associated with a second electrode, $\{x_2, y_2, z_2\}$, $d\vec{x}_{1,2} = \{x_1-x_2, y_1-y_2, z_1-z_2\}$. The square of the length of the vector $d\vec{x}$, along with the square of the known inter-electrode spacing between those electrodes ds, can be used to determine the so-called metric tensor $g_{ij}(x)$, which characterizes the intrinsic geometry of the electrical field used for location measurements at a point x, according to the following set of equations:

$$ds^2 = \sum_{i=1}^{3} \sum_{j=1}^{3} g_{ij}(x) dx^i dx^j. \quad (10)$$

For brevity, equation (10) is often written without the summation signs, which are implied over the repeating upper and lower indices (Einstein's convention):

$$ds^2 = g_{ij}(x) dx^i dx^j. \quad (11)$$

The metric tensor $g_{ij}$ is a symmetric 3×3 matrix:

$$\begin{bmatrix} g_{1,1} & g_{1,2} & g_{1,3} \\ g_{2,1} & g_{2,2} & g_{2,3} \\ g_{3,1} & g_{3,2} & g_{3,3} \end{bmatrix}$$

Because $g_{ij}$ is symmetric, $g_{1,2}=g_{2,1}$, $g_{1,3}=g_{3,1}$, and $g_{2,3}=g_{3,2}$. Accordingly, $g_{ij}$ has six (6) independent components that must be solved.

Generally speaking, for a curved coordinate system, such as one defined by intra-body electrical currents, a metric tensor depends on the location in space at which it is determined—i.e., a metric tensor determined for one location in the coordinate system may not be equal to a metric tensor determined for a different location in the coordinate system. A metric tensor can be computed if the known inter-electrode spacings ds are known for sufficient number of linearly independent spacing measurements at each spatial location, so that equation (11) can be solved.

Global Metric Tensor Computation. Without the correction provided by a metric tensor, the distance between two electrodes (i.e., an inter-electrode spacing) can be defined as:

$$\sum_{i=1}^{3} \sum_{j=1}^{3} \delta_{i,j} dx^i dx^j, \quad (12)$$

where $\delta_{ij}$ is the Kronecker delta, which is defined by the following equations (similar to the definition above):

$\delta_{ij} = 1$, if i=j $\delta_{ij} = 0$, if i≠j

The inter-electrode spacings as defined by equation (12) are seen by a user of the navigation system when a catheter is visualized using the native coordinate system coordinates {x,y,z}. As was mentioned above, in these coordinates the catheter and intracardiac geometry may appear distorted.

A metric tensor is associated with a particular point in space, rather than with an area or volume. In practice, it is not possible to perform enough measurements to determine the metric tensor at all spatial locations, and certain approximations may be employed. Even for a single location, to solve equation (11), six (6) independent distance measurements must be made. For an approximate determination of the metric tensor in a volume, all available distance measurements performed in that volume can be combined as if measured at a single spatial point corresponding the center of the volume. If the volume is small, so that the electrical fields in it are nearly homogeneous, the single metric tensor will provide a good characterization of the volume geometry.

As a substitute for finding metric tensors for all locations in the navigational space, a single metric tensor can be defined for the entire space based on data points collected throughout the space. This metric tensor is referred to herein as a "global metric tensor." The global metric tensor $g_{ij}$ provides a global correction of the native coordinate system. Determining the global metric tensor can be the first sub-step in the step 54 of determining a global transformation.

The global transformation can be treated as a linear transformation. Thus, the global transformation may assume that the electrical fields for positioning and navigation are homogeneous, but that the axes based on those electrical fields are not at 90 degrees to each other and that the proper scales of the coordinate axes are not known. A goal of the global correction is to restore an orthonormal coordinate system.

In an embodiment of the first method 50 used for a procedure on a patient's heart, a subset of the measured electrode positions and measured inter-electrode spacings within the most prominent heart chambers can be used. If chamber-specific information is not available, then data from the entire navigational space can be used, or a subset of data which passes a certain criteria. The criteria may be imposed to include measured positions which are representative of the global geometry, as opposed to some locally distorted features, as will be further explained below.

The set of electrode positions collected in the geometry collection step that are selected for the global metric tensor computation can be defined as $\{\vec{x}_k\}$. The set of inter-electrode spacing vectors connecting closely spaced electrodes on the catheter can be defined as $\{d\vec{x}_k\}$, and the corresponding set of known, pre-determined inter-electrode spacings can be defined as $\{ds_k\}$. Here k=1, . . . , N, for N collected data points. For each data point the following equation holds:

$$(ds_k)^2 = g_{ij}(x)(dx_k)^i(dx_k)^j, \quad (13)$$

k=1, . . . , N, where again the summation is assumed over the repeating indices i and j. Equation (13) is not truly global, however, since the metric tensor is associated with a particular point in the navigation space. Applying equation (13) to the set of collected data points gives a system of numerous equations for the six (6) independent components of the metric tensor.

In the global approximation, the metric tensor in equation (13) can be assumed to be independent of x, which leaves a system of many equations (as many as data points are included into the computation) for just six (6) tensor components. In some embodiments, the equations can be solved by finding the best quadratic fit using the method of pseudo-inverse, which can be performed using the singular value decomposition, as is known in the art. In this approach the following error is minimized:

$$\varepsilon = \sum_{k=0}^{N}((ds_k)^2 - g_{ij}(dx_k)^i(dx_k)^j)^2. \quad (14)$$

The solution to the minimization problem of. equation (14) yields the metric tensor which characterizes the intrinsic geometry of the navigational electrical fields. Approaches for solving error minimization problems, such as the problem of equation (14), are known in the art.

Reconstruction of the Global Coordinate System. The next sub-step in the step 54 of determining a global transformation function can be to define a global transformation function according to the global metric tensor. The global transformation treats the native coordinate system as linear, albeit inappropriately skewed and scaled. Accordingly, the transformation from the native coordinate system to the global coordinate system is linear.

A general linear affine transform in 3-dimensional space contains twelve (12) independent parameters, including nine (9) coefficients and three (3) translations, while the metric tensor only contains six (6) independent quantities. Therefore, the orientation as well as the origin of the global coordinate system are not fixed by the global metric tensor equations and may be chosen based on convenience. In an embodiment, the orientation of the global coordinate system may be chosen so that the X-axis orientation coincides with the general direction of the electrical field defining the x coordinate, and the XZ plane of the global system coincides with the xz plane of the electrical fields. In such an embodiment, the Y-axis also will have the same orientation as the y-axis of the native coordinate system, but the Z-axis may have a different orientation than the z-axis of the native coordinate system. Of course, other orientations of the global coordinate system may be selected. The origin of the global coordinate system also can be chosen arbitrarily. In an embodiment, the origin of the global coordinate system can be coincident with the origin of the current-based coordinate system.

The following is the most general coordinate transformation which satisfies the above criteria concerning the orientation and origin of the global coordinate system:

$$X^1 = C_1^1 x^1 + C_2^1 x^2 + C_3^1 x^3 \quad (15)$$

$$X^2 = C_2^2 x^2 \quad (16)$$

$$X^3 = C_2^3 x^2 + C_3^3 x^3 \quad (17)$$

After solving the values of the transformation coefficients $C_1^1$, $C_2^1$, $C_3^1$, $C_2^2$, $C_2^3$, and $C_3^3$, equations (15)-(17) can be used as a global transformation to relate coordinates in the native coordinate system of the navigation system to the global coordinate system. The coordinate transformation (15)-(17) contains six (6) parameters, the same number as the global metric tensor.

Because the global coordinate system is orthonormal, for each data point the left side of equation (13) can be written as $$(ds)^2 = \delta_{ij} dX^i dX^j = \sum_{i=1}^{3} dX^i dX^i, \quad (18)$$

where again dX denotes a vector connecting closely spaced electrodes on the same catheter. Taking differentials of both sides of equations (15)-(17) while holding the metric tensor constant, and substituting them into the left hand side of equation (13), using (18) and equating the terms corresponding to different $dX^i dX^j$ pairs, the following system of equations for the transformation coefficients $C_1^1$, $C_2^1$, $C_3^1$, $C_2^2$, $C_2^3$, and $C_3^3$ results:

$$(C_1^1)^2 = g_{11}$$

$$C_2^1 C_2^1 = g_{12}$$

$$(C_2^1)^2 + (C_2^2)^2 + (C_2^3)^2 = g_{22}$$

$$C_1^1 C_3^1 = g_{13}$$

$$C_2^1 C_3^1 + C_2^3 C_3^3 = g_{23}$$

$$(C_3^1)^2 + (C_3^3)^2 = g_{33} \quad (19)$$

The system of equations (19) can be readily solved. The full solution contains eight cases. Only one of those cases, though, corresponds to the positive-definite metric tensor and transformation into the coordinate system with the same chirality as the native coordinate system, which is given by the following expressions:

$$C_1^1 = \sqrt{g_{11}} \quad (20)$$

$$C_2^1 = \frac{g_{12}}{\sqrt{g_{11}}}$$

$$C_3^1 = \frac{g_{13}}{\sqrt{g_{11}}}$$

$$C_2^2 = \frac{\sqrt{-g_{11}(g_{23})^2 - g_{22}(g_{13})^2 - g_{33}(g_{12})^2 + g_{11}g_{22}g_{33} + 2g_{12}g_{13}g_{23}}}{\sqrt{-(g_{13})^2 + g_{11}g_{33}}}$$

$$C_2^3 = \frac{-g_{12}g_{13} + g_{11}g_{23}}{\sqrt{g_{11}}\sqrt{-(g_{13})^2 + g_{11}g_{33}}}$$

$$C_3^3 = \frac{\sqrt{-(g_{13})^2 + g_{11}g_{33}}}{\sqrt{g_{11}}}$$

Thus, equations (15)-(17) and (20) provide a global transformation of the electrical current-based coordinate system to the orthonormal global coordinate system, based on the global metric tensor.

Once equations (15)-(17) and (20) are fully defined, the first method 50 can continue to the step 56 of determining the location of a positioning electrode in the native coordinate system. The positioning electrode can be one of the electrodes used in the geometry collection step 52, or it can be a separate electrode on the same catheter or on another catheter.

Once the location of an electrode in the native coordinate system is determined, the first method 50 can continue to a step 58 of applying a global transformation function to the determined location to find corresponding coordinates in the global coordinate system. In an embodiment, the step can include applying equations (15)-(17) and (20) to the determined location to find coordinates in the global coordinate system.

In operation, steps 52 and 54 can be performed once, then steps 56 and 58 can be repeated for every position measurement taken by the navigation system, substantially in real-time. Thus, the navigation system can display the position of one or more electrodes on a catheter in the global coordinate system, advantageously allowing for more accurate guidance and navigation.

As noted above, the global transformation function embodied by equations (15)-(17) and (20) does not take into consideration that the native coordinate system is curved and inhomogeneous. Accordingly, a further method may include one or more local transformations to account for such inconsistencies.

FIG. 5 is a flowchart illustrating a second method 60 for determining the position of a medical device by scaling and correcting a first coordinate system to find coordinates in a second coordinate system. The second method 60 can begin with the same first two steps 52, 54 as the first method 50: a step 52 of collecting data points in global space with a plurality of sensors in a first coordinate system, and a step 54 of determining a global transformation function according to measured distances and known distances between sensors. The second method 60 can then continue to a number of steps to, among other things, correct for any variations and inconsistencies in the local geometry.

Local Geometry Correction. The global transformation function determined in step 54, while providing correction to the major distortions in the native coordinate system, does not provide appropriate maps around local geometric features, which may arise due to impedance differences in and around various anatomical structures, such as tubular blood vessels. In an embodiment, a catheter positioned within a blood vessel in the native coordinate system may "look" stretched (based on position measurements of electrodes on the catheter) compared to a catheter located in a heart chamber. Thus, local geometry corrections, which can be obtained by considering geometry in the vicinities of the structures involved, can be implemented in certain embodiments.

Subdivision of Space Into Volume Elements And Definition of Volume Element Centers. The next step in the second method 60 (and the first step in the correction of local geometry) can be a step 62 of dividing the space covered by the global coordinate system (or a portion thereof) into a plurality of local volumes, each of which comprises a portion of the space covered by the global coordinate system. Measured electrode positions collected in the geometry collection step and associated measured inter-electrode spacings can be assigned to local volumes (for further steps of the second method 60) after the global transformation is applied to those positions and spacings.

In an embodiment, the reference frame for space subdivision can be rotated so that the rotated coordinate axes coincide with the principal axes of the collected data point cloud. This rotation does not change the coordinate axes for the remainder of the algorithm, but is instead only for the purpose of dividing up space into local volume elements. The principal axes can be found by the Principal Component Analysis (PCA), a technique known in the art, that can be performed using the Singular Value Decomposition (SVD). The SVD is also well known in the art, but a brief description is provided below.

Given a matrix p, the singular value decomposition of the matrix is defined as the decomposition into three matrices U, S and V:

$$USV^T = p \quad (21)$$

where U and V are orthogonal and S is diagonal. The orthogonal matrix U contains information about the principal axes of a rotated coordinate system and provides the rotational matrix to the principal axes of the rotated coordinate system from the non-rotated coordinate system. The diagonal matrix S contains the singular values. The orthogonal matrix V contains the relative weights of different data points' contributions to the corresponding principal components.

After rotating the coordinate axes for space subdivision, the navigation domain boundaries can be defined in each dimension as the ranges occupied by position measurements, and then can be divided into a fixed number of sub-domains. In an embodiment, the navigation space can be divided into parallelepipeds.

The smaller the size of each local volume, the higher the resolution of the resulting scaling algorithm. On the other hand, a higher number of local volumes requires more computation for some steps of the second method 60. In practice, only a fraction of the local volumes may actually contain data points, allowing for efficient computational strategies. In an embodiment, the number of subdivisions for each axis may be ten (10) (for 1,000 total local volumes). In an embodiment in which the data point cloud is collected in and around a human heart, ten (10) subdivisions per axis may correspond to a parallelepiped side length of about 10 mm. Such a local volume size may provide a good compromise between computational efficiency and algorithm resolution. Of course, larger or smaller local areas are possible, and are contemplated.

After the initial subdivision of the navigational domain, the local volumes can be defined for each parallelepiped as an ellipsoid with a diameter in each direction that exceeds the size of original parallelepiped's side, leading to overlapping volume elements. In an embodiment, the overlap factor—i.e., the amount by which a diameter of an ellipsoid can exceed the size of the corresponding paralleliped—can be two (2). In other embodiments, larger or smaller overlap factors can be used, and the algorithm and methods herein are not restricted to a particular overlap factor. The "center" of each local volume (which may be used in later steps of the second method 60) can be defined as mean locations of the position measurements within the local volume ellipsoid. Empty local volume elements (i.e., without any position measurements from the geometry collection step 52) can be dropped from further computation.

Local Metric Tensor Computation. Once local volumes are defined and position measurements are assigned to the local volumes, the second method 60 can continue to the step 64 of determining a local transformation function for each local volume according to the collected data points within that local volume. In an embodiment, the local transformation function can include a local metric tensor. The local metric tensor may be computed for each local volume in a manner similar to the computation of the global metric tensor described above in the global transformation step 54. In an embodiment, additional computation (i.e., in addition to the computation described in step 54) may be required if the collected data in a local volume element is insufficient to determine all portions of the transformation function (i.e., all six (6) independent components of a metric tensor) for that local volume. An example of such additional computation is described below.

As noted above, a metric tensor contains six (6) independent components, so the system of equations generated by equation (14) is only fully defined when at least six (6) linearly independent data points are available within the relevant local volume. However, even in the case when more than six (6) linearly independent data points are available, often not all of the metric tensor components can be reliably defined due to noise, which can make degenerate data appear non-degenerate. To account for possible noise in data, certain volume elements may be eliminated from further computation. For example, volume elements may only be included in further computation if they contain a minimum number of data points such as, for example only, six data points.

Even if all components of a metric tensor cannot be calculated, there may be enough data to recover and utilize parts of the metric tensor. In an embodiment, the metric tensor components which can be resolved based on the available data can be found, and the subspace orthogonal to it can be left unscaled, by setting the corresponding diagonal components of the metric tensor matrix to one (1) and off-diagonal components to zero (0). This is accomplished, for example, by using the Principal Component Analysis (PCA) by means of the Singular Value Decomposition (SVD). The singular values generated by the SVD will contain information about the levels of data degeneracy.

To determine the level of data degeneracy, the principal axes in the space of the inter-electrode vectors $\{d\vec{x}_k\}$ can first be found, where k spans the data points in the local volume element under consideration. The volume element's local coordinate system can be rotated to the principal axes of the position measurements within the local volume element, using the PCA, as described above.

A matrix m may be used for determining data degeneracy, and may be defined as:

$$m^{ij} = \sum_k (dx_k)^i (dx_k)^j, \qquad (22)$$

where k runs over all vectors within the volume element. The matrix U which, as discussed above, provides the rotational matrix to the principal axes of the underlying data, can be generated by the SVD of the matrix m, and can then be used to rotate each of the inter-electrode spacing vectors belonging to the local volume to the principal axes-based coordinate system:

$$(dx_k)^{i'} = U_{i'i}(dx_k)^i. \qquad (23)$$

The metric tensor can then found in the rotated local coordinate frame using equation (14).

In the rotated local coordinate frame, the local metric tensor may be diagonal. This follows from differential geometry considerations, based on the fact that the so-called covariant components of the metric tensor $g_{ij}$ are given by the scalar products of the basis vectors of the reference frame, which is defined by local measurements, and is explicitly orthogonal after the rotation performed in equation (23). The diagonal elements of the diagonal metric tensor are the squares of the scale corrections for the corresponding axes.

However, as mentioned above, some of the metric tensor components may not be unambiguously determinable from the available data (i.e., due to data degeneracy). In this case, a significant disparity among the singular values, which are located on the diagonal of the matrix S generated by the SVD in equation (21), may be present. To find the disparity, two numbers $r_1$ and $r_2$ can be computed from the diagonal elements of the matrix S:

$$r_1 = S_{22}/S_{11} \qquad (24)$$

$$r_2 = S_{33}/S_{22} \qquad (25)$$

If $r_1$ is smaller than some threshold, then the data in the local volume may be effectively one-dimensional, and only $g_{1'1'}$ is retained for the local metric tensor, while all other diagonal components of the local metric tensor are set to one (1) and off-diagonal components are set to zero (0). If only $r_2$ is smaller than the threshold, then $g_{3'3'}=1$, and $g_{3'j'}=0$, while the computed values of the $g_{i'j'}$ components with i', j'=1,2 are retained. Again, primes are used to denote computation in the rotated local coordinate system. The threshold can be determined experimentally and may depend on the data quality. In an embodiment, the threshold can be about 0.07.

Once the local metric tensor $g_{i'j'}$ is computed, it is rotated into the original reference frame using the same orthogonal (but effectively transposed) matrix U:

$$g_{ij}=U_{ii'}U_{jj'}g_{i'j'}. \quad (26)$$

Solving equation (26) gives the values of the local metric tensor of a local volume element. Thus, equations (22)-(26) can be solved for each local volume element in step 64 for which there is insufficient data to compute all six (6) independent components of the local metric tensor. As noted above, equation (14) can be solved for each local volume for which there is sufficient data to determine all independent components of the local metric tensor.

Although not described above in the global transformation step 54, the approach of determining only a portion of the metric tensor could be used for the global metric tensor as well, since there is no guarantee a priori that the global data set is not degenerate.

The upper and lower indices used in equations (21), (23) and (26) may appear to be mismatched. However, the calculation of equation (26) can be performed in a reference frame in which the global metric tensor is given by the Kronecker's delta $\delta_{ij}$. In such a reference frame, there is no practical difference between the upper and lower indices. Using the global metric tensor in this way, however, amounts to retaining the greatest terms in the implicit Taylor series expansion over deviations from the global homogeneous geometry, in which corrections from the local metric tensors are relatively small. This implicit assumption may not be true in all areas of the navigation domain. If it is not true, the matrix U may not rotate exactly to the principal axes, but to different axes separated from the principal axes by unknown angles. In such a case, the local metric tensor may have non-diagonal elements that are non-zero and singular values that do not exactly reflect the level of degeneracy. However, such effects will typically be negligible.

Discarding Certain Local Volume Elements. After the local transformation functions (i.e., the local metric tensors) of the local volumes have been computed in step 64, the second method 60 can continue to a step 66 of discarding any local volume from further processing for which the local transformation function scales too much or too little. The collected data quality could be different in different local volumes, so some of the computed local metric tensors could be non-positive definite, or lead to excessive scaling of the corresponding volumes. The amount of scaling can be determined with reference to the determinant of the local metric tensor matrix.

Denoting the determinant of the local metric tensor as g in the global coordinate system and g' in the local coordinate system resulting from application of the local metric tensor, and denoting the volume of the local volume elements as dV in the global coordinate system and dV' in the local coordinate system, the volume scale is related to the determinant of the metric tensor in the following way:

$$\sqrt{g'}dV'=\sqrt{g}dV, \quad (27)$$

where by definition $$g=det(g_{ij}). \quad (28)$$

The value of g defines the amount of the volume scaling; a goal of the algorithm is to find the local coordinate system in which g'=1. Accordingly, one way to determine if a local metric tensor overscales or underscales is to discard local volume elements for which g is too large or too small.

From equation, (27) it follows that g must be a positive number. If g is too large or too small, the data likely contains excessive inconsistencies. Accordingly, g can be compared to upper and lower thresholds, and local volume elements for which g is larger than the upper threshold or lower than the lower threshold can be dropped from further computation. The upper and lower thresholds can be determined experimentally. In an embodiment, upper and lower thresholds may be selected such that:

$$0<g<100. \quad (29)$$

Volume Element Center Triangulation. The second method 60 can continue to a step 68 of finding edges connecting the centers of neighboring local volumes. In an embodiment, this step can include the use of a triangulation algorithm such as, for example, Delaunay triangulation. In other embodiments, other triangulation methods or other methods for connecting neighboring volume elements may also be used. The step can also include discarding certain edges such as, for example, edges longer than a certain threshold. In an embodiment in which the step 68 is used on data collected in and around a human heart, a threshold of two (2) mean distances between neighboring local volume centers may be used. Discarding such edges can avoid connecting distant local volumes (e.g., distant cardiac structures) and can minimize the number of edges connecting local volume elements separated by space without data points.

Relaxation of Inter-Volume Distances. Once the edges connecting neighboring local volume elements have been found, the second method 60 can continue to a step 70 of shifting the centers of the local volumes along the connecting edges. The shifting step 70 may shift the centers of the local volumes to their locations in the corrected coordinate system. In an embodiment, the shifting step 70 can include the use of a relaxation algorithm.

Conceptually, the relaxation algorithm may be similar to releasing (i.e., relaxing) compression or tension from a number of connected springs, in which the edges connecting local volumes are the springs. The local volume element centers can be conceived as being physically moved from their locations in the global coordinate system to their measured locations in the native coordinate system. This movement results in compression or expansion of the edges connecting neighboring local volume elements. The relaxation algorithm conceptualizes the edges as springs, and allows the springs to relax.

The tension or compression on each spring (i.e., edge) can be evaluated by comparing (1) the lengths of the edges connecting volume centers at their locations in the global coordinate system with (2) the lengths of the edges computed using the local metric tensors determined in step 64. Since each edge connects the centers of two volumes, in an embodiment, an average of the local metric tensors for the two local volumes connected by the edge are used. Treating the edges as vectors, forces acting on the centers of the volumes can be defined as vector sums of the individual springs' forces.

The relaxation proceeds iteratively in relatively small steps, so that the forces acting on each volume center move that center towards its equilibrium by a certain length based on the force value. The final locations of the centers of the local volumes in the corrected coordinate system are found by performing iterations until a certain criteria is satisfied.

The locations of the centers of the volume elements at iteration t in the relaxation algorithm can be denoted $\vec{X}^k(t)$. At iteration t=0, these locations are the same as the original locations. As t increases, the local volume centers move toward their equilibrium locations.

In an embodiment, a volume center k be connected with $n^k$ neighbors by vectors $\vec{l}^i(t)$, each vector having the length $|\vec{l}^i(t)|$ in the native coordinate system and length $|\vec{L}^i(t)|$ computed with the metric tensor. The volume center can then be moved to a new location along the vector in equation (30) below:

$$\sum_{i=1}^{n^k} \frac{\vec{l}^i(t)}{|\vec{l}^i(t)|} \frac{(|\vec{L}^i(t)| - |\vec{l}^i(t)|)}{|\vec{L}^i(t)|}, \tag{30}$$

in which each contribution to the sum comes from a "spring" stretched or compressed along the corresponding vector. The first fraction within the sum represents the unit vector along the line connecting two local volume centers (i.e., a direction of the net "force" on a volume center), while the second fraction describes the strain of the corresponding spring (i.e., a magnitude of the net "force"). The move is performed in the direction reducing the force on the volume center which is being moved.

At each iteration of the relaxation algorithm, each local volume center will be moved to a new location defined as:

$$\vec{X}^k(t+1) = \vec{X}^k(t) + \alpha(t) \sum_{i=1}^{n^k} \frac{\vec{l}^i(t)}{|\vec{l}^i(t)|} \frac{(|\vec{L}^i(t)| - |\vec{l}^i(t)|)}{|\vec{L}^i(t)|}, \tag{31}$$

where $\alpha(t)$ is a "spring" constant used at the t iteration step. As soon as a new value $X^k(t+1)$ is computed, that new value may be used in further computation, even during the current iteration cycle.

The spring constant $\alpha(t)$ determines the rate of convergence and algorithm stability. Therefore, it is important to select spring constants that are large enough for relatively quick convergence, but small enough for the relaxation algorithm to be stable. Proper spring constants can be determined experimentally. In an embodiment, the spring constant $\alpha(t)$ can be reduced at each iteration step to ensure stability of the relaxation algorithm. For example, a slow exponential decrease of $\alpha(t)$ can be used according to the following formula:

$$\alpha(t) = \alpha(1) e^{-(t-1)/60}, \tag{32}$$

where $\alpha(1)$ is the value of the spring constant at the first iteration. In an embodiment, $\alpha(1)$ can be about 1. The relationship shown in equation (32) is not the only possible way to decrease the spring constant, but is simple and may effectively enforce a limit on the number of iterations of about 100.

The computation is stopped when the total displacement of the volume centers becomes smaller than a certain value:

$$d(t+1) = \sum_{k=1}^{n} \left| \vec{X}^k(t+1) - \vec{X}^k(t) \right|, \tag{33}$$

$$d(k+1) < d_{min}, \tag{34}$$

where n is the number of local volume centers included into the computation. The constant $d_{min}$ is determined based on desired accuracy and computational efficiency. In an embodiment, $d_{min}$ can be selected such that $d_{min} = 0.05 \times n$ mm. In practice, $d_{min}$ may limit the number of iterations to about 30, while stopping the algorithm when the average correction for each volume center per iteration step falls bellow 0.05 mm. In addition, a hard stop on the number of iterations can be imposed in order to prevent the system from spending too much time on the computation.

In an embodiment, the effects of the relaxation algorithm on the coordinate system transformation may be most significant for portions of the coordinate system in which elongate structures, such as blood vessels, are present. In such structures, the tissue and blood impedance distributions may cause a catheter to appear more elongated than it is, which manifests itself in the measured inter-electrode spacings being larger than in cardiac chambers. Therefore, in intracardiac geometry applications, local geometry correction generally makes the largest changes in the corrected coordinate system in blood vessels.

Interpolation. After shifting the centers of the local volumes, the second method 60 can continue to a step 72 of determining an interpolation function according to the locations of the centers of the volume elements in the native coordinate system and as a result of the shifting step 70. The interpolation function can map the entire native coordinate system to a corrected coordinate system.

One interpolation algorithm that can be used to build the interpolation function is the Thin Plate Splines algorithm, though other appropriate interpolation algorithms known in the art may also be used. The Thin Plate Splines algorithm accepts so-called fiducial pairs as input. In an embodiment, the fiducial pairs can include (a) locations of the local volume element centers in the native coordinate system $\{x,y,z\}$ and (b) the locations of the local volume element centers in the corrected coordinate system $\{X,Y,Z\}$ (as determined in the shifting step 70). Given N total local volume centers in the corrected coordinate system, the fiducial pairs input to the algorithm are:

$$\{\vec{x}_k, \vec{X}_k\}, k, \ldots, N. \tag{35}$$

where again vector notation is used to denote three-dimensional points in both the native and corrected coordinate systems.

The map from the electrical current-based coordinate system into the corrected coordinate system (which may be orthonormal) is represented by the following three functions, where $\vec{x} = \{x,y,z\}$ and $\vec{X} = \{X,Y,Z\}$:

$$X(x, y, x) = b^{xx}x + b^{xy}y + b^{xz}z + c^x + \sum_{j=1}^{N} a_j^x \psi_j(\vec{x}) \tag{36}$$

$$Y(x, y, x) = b^{yx}x + b^{yy}y + b^{yz}z + c^y + \sum_{j=1}^{N} a_j^y \psi_j(\vec{x})$$

$$Z(x, y, x) = b^{zx}x + b^{zy}y + b^{zz}z + c^z + \sum_{j=1}^{N} a_j^z \psi_j(\vec{x})$$

where the numbers $a_j^x$, $a_j^y$, $a_j^z$, $b^{xi}$, $b^{yi}$, $b^{zi}$ and $c^x$, $c^y$, $c^z$, j=1, ..., N, i=x,y,z are (initially-unknown) coefficients for which values must be determined, and $\Psi_j(\vec{x})$ is a three-dimensional basis function. The basis function $\Psi_j(\vec{x})$ may be selected from a range of the radial basis functions. The exact form of the basis function may be selected according to the dimensionality of the spline (the spline described in step 72 is three-dimensional for the algorithm described herein). One set of radial basis functions that may be used is the Euclidean distance as set forth in equation (37) below:

$$\Psi_j(\vec{x}) = \sqrt{(x-x_j)^2 + (y-y_j)^2 + (z-z_j)^2} \quad (37)$$

which may be expressed in short form as in equation (38) below:

$$\Psi_j(\vec{x}) = |\vec{x} - \vec{x}_j| \quad (38)$$

The above equation set (36) represents a system of 3N+12 linear equations for 3N+12 unknowns. This is because the summation term in each of the three equations in equation set (36) includes N unknowns, yielding 3N unknowns in total. Moreover, each of the three equations in equation set (36) has four additional terms with a respective unknown coefficient, yielding twelve (12) more unknowns arising from these additional terms. The total number of equations/unknowns is thus 3N+12. Applying the above functions (38) requires first solving for the 3N+12 coefficients.

Solving for the unknown coefficients may include a smoothing parameter λ, which controls how close the corrected coordinates $\vec{X} = \{X,Y,Z\}$ are to the current-based coordinates $\vec{x} = \{x,y,z\}$. If λ is set to zero, the corrected coordinate system output (i.e., interpolation function output) for each native coordinate system input is equal to the corrected coordinate system data point in a fiducial pair with that current-based coordinate system data point. A non-zero λ results in a smoother solution by avoiding over-fitting noisy measurements in the fiducial pairs. The value of λ may vary from procedure to procedure and/or from system to system. In general, λ may be a number greater than zero determined through routine experimentation to strike a proper balance between accurately reflecting the results of the rest of the second method 60 and avoiding over-fitting noisy data. λ may have a value relative to the number of fiducial pairs. For example, in an embodiment, λ may be assigned the value 0.025N, where N is the number of fiducial pairs (e.g., such that λ=5 for N=200). Implementing λ and setting equations (36) in an iterative form to solve for the 3N+12 coefficients results in the following set of equations (39) and (40):

$$X_k = b^{xx}x_k + b^{xy}y_k + b^{xz}z_k + c^x + \sum_{j=1}^{N} a_j^x(\psi_j(\vec{x}_k) - \lambda\delta_{jk}), \quad (39)$$

$$Y_k = b^{yx}x_k + b^{yy}y_k + b^{yz}z_k + c^y + \sum_{j=1}^{N} a_j^y(\psi_j(\vec{x}_k) - \lambda\delta_{jk}),$$

$$Z_k = b^{zx}x_k + b^{zy}y_k + b^{zz}z_k + c^z + \sum_{j=1}^{N} a_j^z(\psi_j(\vec{x}_k) - \lambda\delta_{jk}),$$

$$\sum_{k=1}^{N} a_k^i = 0, \sum_{k=1}^{N} a_k^i x_k = 0, \sum_{k=1}^{N} a_k^i y_k = 0, \quad (40)$$

$$\sum_{k=1}^{N} a_k^i z_k = 0, i = x, y, z,$$

Like equation set (36), modified equation set (39) is a set of 3N+12 equations that includes 3N+12 unknowns. Equations (39) and (40) can be solved (e.g., by logic 36) to find the 3N+12 unknown coefficients for equation set (39), whose values may be stored as coefficients (e.g., in memory 32). To solve equations (39) and (40), the fiducial pairs $\{\vec{x}_k, \vec{X}_k\}$, k, . . . , N. are used. Several different approaches known in the art, including software-based approaches, can be used to solve a number of equations with the same number of unknowns, and accordingly, can be used to determine the respective values for the unknown coefficients.

As described above, the fiducial pairs are used to solve for the unknown coefficients in equation sets (39) and (40) so that those coefficients may be applied in equation set (36)—that is the first purpose of the fiducial pairs. The fiducial pairs—or, more specifically, the native coordinate system coordinates $\{\vec{x}_k\}$ in the fiducial pairs—also have a distinct second purpose: continuous use in real-time application of equation set (36). Accordingly, the native coordinates in the fiducial pairs can be stored in a reference coordinates data structure for use in the summation portion of equations (36) in real-time operation, such as geometry file 34.

Real-Time Application. Once the interpolation function has been determined in the interpolation function step 72, the second method 60 can include additional steps to permit real-time applications such as, for example, the real-time navigation of a catheter within a body. The next step 74 can include determining the location of at least one electrode in the native coordinate system. The electrode can be one of the electrodes used in the geometry collection step 52, another electrode on the same catheter, or an electrode on a different catheter entirely.

The second method 60 further includes a step 76 of applying the interpolation function (e.g., as embodied in equation set 36) to the location determined in the native coordinate system to find corresponding coordinates in the corrected coordinate system. Applying the interpolation function may involve the use of stored reference coordinates, e.g., stored native coordinate system coordinates, as noted above. Steps 74 and 76 can be applied continuously, to a plurality of electrode positions, to enable navigation of a catheter in the corrected coordinate system substantially in real time.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for determining the position of a medical device including a first impedance-based position sensor and a second impedance-based position sensor, the method comprising:
   detecting a plurality of respective positions, in a global space, of the first impedance-based position sensor and the second impedance-based position sensor in a first, non-orthonormal coordinate system associated with a current-based electrical field;
   measuring a plurality of distances between said respective positions;
   determining a global transformation function using the measured distances between said respective positions;
   dividing the global space into a plurality of local volumes based on the measured distances between said respective positions;
   determining a local transformation function for each local volume according to a known distance between the first sensor and the second sensor and according to said measured distances between said respective positions;
   applying said local transformation function to said detected respective positions of the first sensor and the second sensor in the first coordinate system to:
      determine corresponding respective positions of the first sensor and the second sensor in a second, orthonormal, coordinate system, and
      correct for local inconsistencies and variations in the respective positions of the first sensor and the second sensor in the first coordinate system; and
   based on the respective positions of the first sensor and the second sensor in the second, orthonormal, coordinate system, guiding navigation of the medical device to a treatment site.

2. The method of claim 1, wherein the medical device is a first medical device, the method further comprising:
   detecting a position of a third sensor coupled to a second medical device in said first coordinate system; and
   applying said transformation function to said detected position of the third sensor to relate said detected position of the third sensor to said second coordinate system.

3. The method of claim 2, wherein the first medical device is the second medical device.

4. The method of claim 1, wherein at least one of the first position sensor and the second position sensor is configured to generate an electrical signal indicative of its position for an electrical field-based positioning system.

5. The method of claim 1, further comprising:
   establishing an interpolation function according to said local transformation function;
   receiving a signal from a third sensor indicative of a position of the third sensor within said first coordinate system; and
   applying said interpolation function to said position of the third sensor to determine a position of the third sensor in a third coordinate system.

6. A method for determining the location of a first or second impedance-based position sensor, the method comprising:
   detecting a plurality of respective positions, in a global space, of the first impedance-based position sensor and the second impedance-based sensor in a first, non-orthonormal coordinate system associated with a current-based electrical field;
   determining a global transformation function according to a plurality of position measurements in a first, non-orthonormal coordinate system, associated with a current-based electrical field;
   dividing a portion of a space covered by the first, non-orthonormal coordinate system into a plurality of local volumes based on the plurality of position measurements; determining a local transformation function for at least one of said plurality of local volumes, each local transformation function determined according to a plurality of position measurements in said first coordinate system or a second, orthonormal coordinate system within a respective local volume;
   establishing an interpolation function according to said local transformation function; receiving a signal from the first or second impedance-based position sensor indicative of a position of the first or second impedance-based position sensor within said first coordinate system;
   applying said interpolation function to said position to:
      determine a position of the first or second impedance-based position sensor in the second, orthonormal coordinate system, and correct for local inconsistencies and variations in the position of the first or second impedance-based position sensor in the first coordinate system;
   and based on the respective positions of the first sensor and the second sensor in the second, orthonormal, coordinate system, guiding navigation of medical device to a treatment site.

7. The method of claim 6, wherein said local transformation function is determined further according to a plurality of measured distances between said position measurements.

8. The method of claim 6, wherein said interpolation function is determined according to a thin-plate splines algorithm.

9. The method of claim 6, wherein said step of determining a local transformation function comprises computing a respective local metric tensor for each of said at least one of said plurality of local volumes.

10. The method of claim 6, further comprising a step of finding a weighted center of each of said at least one of said plurality of local volumes according to said plurality of position measurements.

11. The method of claim 10, further comprising a step of finding one or more lines that connect each weighted center to one or more respective neighboring weighted centers.

12. The method of claim 11, wherein said one or more lines are found according to Delaunay triangulation.

13. The method of claim 11, further comprising shifting said weighted centers along said lines.

14. The method of claim 6, further comprising the step of discarding any local transformation function that exceeds a predetermined scaling threshold.

15. A system for determining the location of first and second impedance-based position sensors coupled to a medical device, the system comprising:
   an electronic control unit (ECU) comprising a processor;
   a computer-readable memory coupled to said processor; and
   instructions stored in said memory configured to be executed by said processor, wherein said processor is configured to execute said instructions to:
      detect a plurality of respective positions, in a global space, of the first impedance-based position sensor and the second impedance-based position sensor in a first, non-orthonormal, coordinate system associated with a current-based electrical field;
measure a plurality of distances between said respective positions;
determine a global transformation function using the measured distances between said respective positions;
divide the global space into a plurality of local volumes based on the measured distances between said respective positions;
determine a local transformation function for each local volume according to a known distance between the first sensor and the second sensor and according to said measured distances between said respective positions;
apply said local transformation function to said detected respective positions of the first sensor and the second sensor to:
   determine corresponding respective positions of the first sensor and the second sensor in a second, orthonormal, coordinate system, and
   correct for local inconsistencies and variations in the respective positions of the first sensor and the second sensor in the first coordinate system; and
based on the respective positions of the first sensor and the second sensor in the second, orthonormal, coordinate system, guiding navigation of the medical device to a treatment site.

16. The system of claim 15, wherein said processor is further configured to execute said instructions to:
   detect a position of a third sensor in said first coordinate system; and
   apply said transformation function to said detected position of the third sensor to relate said detected position of the third sensor to said second coordinate system.

17. The system of claim 15, wherein said processor is further configured to execute said instructions to:
   establish an interpolation function according to said local transformation function;
   receive a signal from a third sensor indicative of a position of the third sensor within said first coordinate system; and
   apply said interpolation function to said position of the third sensor to determine a position of the third sensor in a third coordinate system.

18. The system of claim 17, wherein said third coordinate system is orthonormal.

19. The system of claim 15, wherein said second coordinate system is orthonormal.

* * * * *